Figure 1:
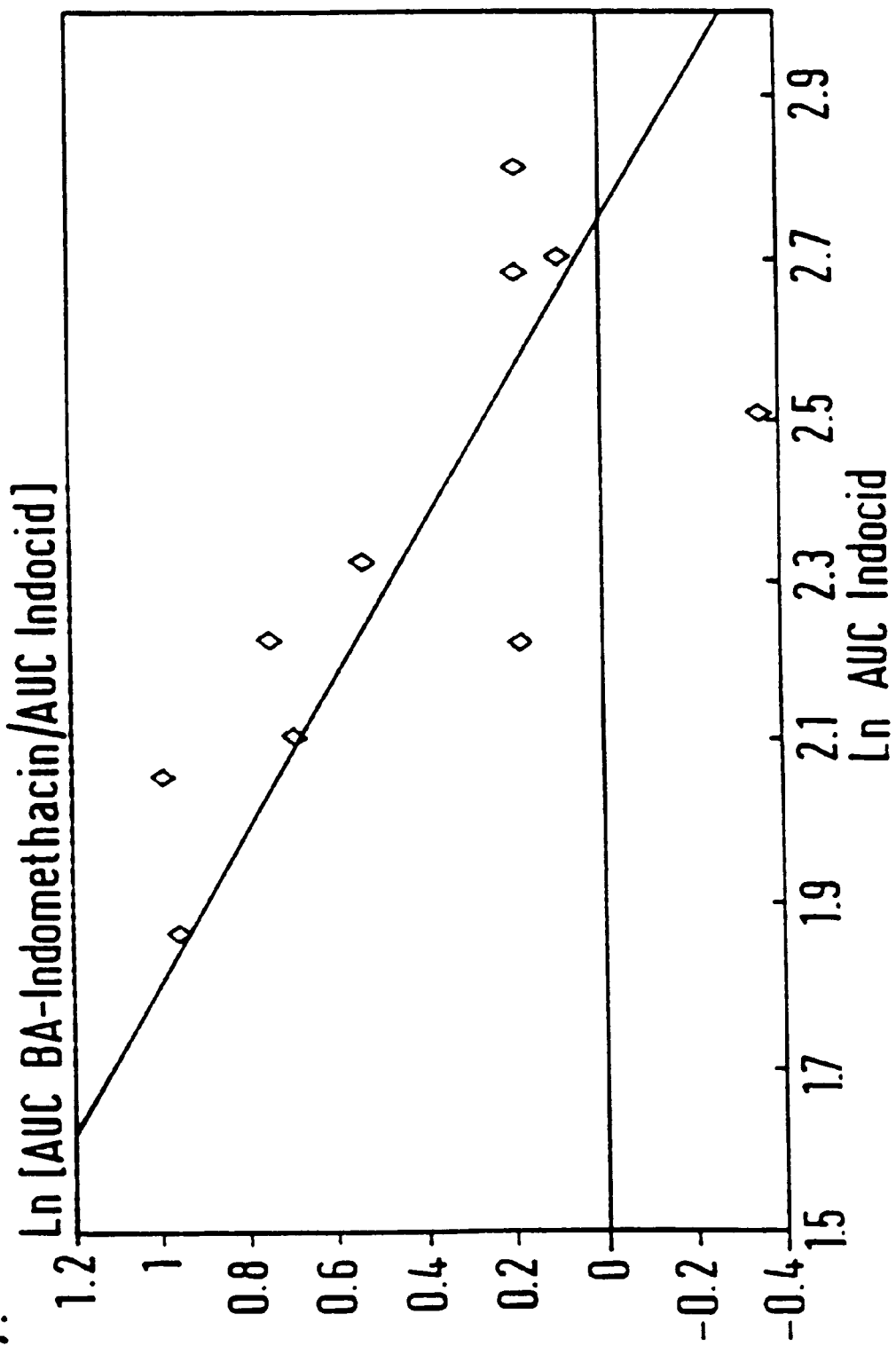

United States Patent [19]
Barnwell

[11] Patent Number: 5,942,248
[45] Date of Patent: Aug. 24, 1999

[54] PHARMACEUTICAL COMPOSITION CONTAINING A LOW DETERGENT EFFECT BILE SALT AND AN ACTIVE COMPOUND THAT UNDERGOES BILIARY EXCRETION AND/OR ENTEROHEPATIC RECYCLING

[75] Inventor: Stephen George Barnwell, Chester, United Kingdom

[73] Assignee: Cortecs Limited, Isleworth, United Kingdom

[21] Appl. No.: 08/338,548

[22] PCT Filed: Jun. 11, 1993

[86] PCT No.: PCT/GB93/01247

§ 371 Date: Feb. 2, 1995

§ 102(e) Date: Feb. 2, 1995

[87] PCT Pub. No.: WO93/25192

PCT Pub. Date: Dec. 23, 1993

[30] Foreign Application Priority Data

Jun. 12, 1992 [GB] United Kingdom .................. 9212511

[51] Int. Cl.⁶ .............................. A61K 9/22; A61K 9/26; A61K 9/52
[52] U.S. Cl. .......................... 424/457; 424/468; 424/469; 424/474; 424/475
[58] Field of Search .................................... 424/458, 474

[56] References Cited

U.S. PATENT DOCUMENTS

| | | | |
|---|---|---|---|
| 4,115,313 | 9/1978 | Lyon et al. .............................. | 252/309 |
| 4,156,719 | 5/1979 | Sezak et al. ............................ | 424/118 |
| 4,164,573 | 8/1979 | Galinsky ................................. | 424/178 |
| 4,263,272 | 4/1981 | Frigerio .................................. | 424/19 |
| 4,447,412 | 5/1984 | Bilton ..................................... | 424/16 |
| 4,579,730 | 4/1986 | Kidron et al. .......................... | 424/19 |
| 4,760,059 | 7/1988 | Behl et al. .............................. | 514/206 |
| 4,795,644 | 1/1989 | Zentner .................................. | 424/468 |
| 4,797,286 | 1/1989 | Thakkar et al. ........................ | 424/456 |
| 4,814,183 | 3/1989 | Zentner .................................. | 424/485 |
| 4,847,092 | 7/1989 | Thakkar et al. ........................ | 424/456 |
| 4,849,227 | 7/1989 | Cho ........................................ | 424/408 |
| 4,880,634 | 11/1989 | Speiser ................................... | 424/468 |
| 4,944,944 | 7/1990 | Tang et al. ............................. | 424/94.6 |
| 4,976,949 | 12/1990 | Meyer et al. ........................... | 424/468 |
| 5,112,619 | 5/1992 | Thakkar et al. ........................ | 424/456 |
| 5,122,127 | 6/1992 | Stanley .................................. | 604/890.1 |
| 5,234,697 | 8/1993 | Sipos ...................................... | 424/490 |
| 5,262,172 | 11/1993 | Sipos ...................................... | 424/490 |
| 5,288,497 | 2/1994 | Stanley et al. ......................... | 424/440 |
| 5,288,498 | 2/1994 | Stanley et al. ......................... | 424/440 |
| 5,300,300 | 4/1994 | Egidio et al. .......................... | 424/456 |
| 5,314,921 | 5/1994 | Yesair .................................... | 514/784 |
| 5,422,124 | 6/1995 | Valducci ................................ | 424/497 |

FOREIGN PATENT DOCUMENTS

| | | |
|---|---|---|
| 0 391 369 | 10/1990 | European Pat. Off. . |
| 230 605 | 9/1989 | New Zealand . |
| 228928 | 11/1991 | New Zealand . |
| 2036558 | 7/1980 | United Kingdom . |
| 90/12583 | 11/1990 | WIPO . |

OTHER PUBLICATIONS

"Physical–Chemical Properties of Bile Acids and Their Salts", *Sterols and Bile Acids* (Elsvier Science Publishers B.V.), 345–403, 1985.

D.E. Duggan et al., "Enterohepatic Recirculation of Drugs as a Determinant of Therapeutic Ratio", Drug Metabolism Reviews, vol. 9, No. 1, pp. 21–41, 1979.

S. Miyazaki et al., "Micellar Interaction of Indomethacin and Phenylbutazone with Bile Salts", Intl. Jour. of Pharmaceutics, vol. 8, pp. 303–310, 1981.

K.C. Kwan et al., "Kinetics of Indomethacin Absorption, Elimination, and Enterohepatic Circulation in Man", Jour. Pharmacokinetics and Biopharmaceutics, vol. 4, No. 3, pp. 255–280, 1976.

K. Miyazaki et al., "Effect of Chenodeoxycholic and Ursodeoxycholic Acids on Isolated Adult Human Hepatocytes", Digestive Diseases and Sciences, vol. 29, No. 12, pp. 1123–1130, 1984.

B. Dordoni et al., "Reduction of Absorption of Paracetamol by Activated Charcoal and Cholestyramine: A Possible Therapeutic Measure", British Medical Journal, vol. 3, pp. 86–87, 1973.

J. Reichen et al., "Cholestasis", *The Liver: Biology and Pathobiology*, Chapter 63, pp. 1105–1124, 1988.

S. Barnwell et al., "Effect of taurochenodeoxycholate or tauroursodeoxycholate upon biliary output of phospholipids and plasma–membrane enzymes, . . . ", Biochem. J., vol. 216, pp. 107–111, 1983.

A. Hofmann, "Bile Acids", *The Liver: Biology and Pathobiology*, Chapter 32, pp. 553–572, 1988.

D.E. Duggan et al., "The Metabolism of Indomethacin in Man", Jour. Pharmacology and Experimental Therapeutics, vol. 181, No. 3, pp. 563–575, 1972.

D.E. Duggan et al., "Enterohepatic Circulation of Indomethacin and its Role in Intestinal Irritation", Biochemical Pharmacology, vol. 25, pp. 1749–1754, 1975.

H.B. Hucker et al., "Studies on the Absorption, Distribution and Excretion on Indomethacin in Various Species", Jour. Pharmacology and Experimental Therapeutics, vol. 153, No. 2, pp. 237–249, 1966.

S. Miyazaki et al., "Interaction of Drugs with Bile Components. II. Effect of Bile on the Absorption of Indomethacin and Phenylbutazone in Rats", Chem. Pharm. Bull., vol. 28, No. 1, pp. 323–326, 1980.

(List continued on next page.)

*Primary Examiner*—Shep K. Rose
*Attorney, Agent, or Firm*—Foley & Lardner

[57] ABSTRACT

Non-steroidal anti-inflammatory drugs, such as indomethacin, and other pharmaceutically active compounds, are formulated with bile acids or their salts and conjugates. Bile acids previously proposed for use in such formulations have placed an unacceptable toxic load on the liver and/or cells of the gastrointestinal tract, causing abnormal liver function or cell erosion. In this invention, the bile acid is a low detergent bile acid, such as ursodeoxycholate. Stabilization of the bile acid pool results in enhanced and predictable enterohepatic recycling of NSAIDs (and other drugs) and a reduced risk of toxicity.

10 Claims, 1 Drawing Sheet

OTHER PUBLICATIONS

S. Miyazaki et al., "Interaction of Drugs with Bile Components. I. Effects of Bile Salts on the Dissolution Behavior of Indomethacin and Phenylbutazone", Chem. Pharm. Bull., vol. 27, No. 10, pp. 2468–2472, 1979.

S. Kanai et al., "Tauro β–Muricholate is as Effective as Tauroursodeoxycholate in Preventing Taurochenodeoxycholate–Induced Liver Damage in the Rat", Life Sciences, vol. 47, pp. 2421–2428, 1990.

R.E. Poupon et al., "A Multicenter, Controlled Trial of Ursodiol for the Treatment of Primary Biliary Cirrhosis", The New England Journal of Medicine, vol. 324, No. 22, pp. 1548–1554, 1991.

E. Rolandi et al., "Effects of ursodeoxycholic acid (UDCA) on serum liver damage indices in patients with chronic active hepatitis", Eur. J. Clin. Pharmacol., vol. 40, pp. 473–476, 1991.

K. Miyazaki et al., "Effect of Chenodeoxycholic and Ursodeoxycholic Acids on Isolated Adult Human Hepatocytes", Digestive Diseases and Sciences, vol. 29, No. 12, pp. 1123–1130, 1984.

A. Esteller et al., "Enhancement of Maximal Bilirubin Excretion by Bile Salts in the Anaesthetized Rabbit", Quarterly Jour. of Experimental Physiology, vol. 69, pp. 217–225, 1984.

K. Kitani et al., "Tauroursodeoxycholate prevents biliary protein excretion induced by other bile salts in the rat", Amer. Jour. Physiology, vol. 248, pp. G407–G417, 1985.

J. Lillienau et al., "Hepatic and ileal transport and effect on biliary secretion of norursocholic acid and its conjugates in rats", Amer. Jour. Physiology, vol. 261, pp. G1057–G1064, 1991.

C.O. Abernathy et al., "Drug–Induced Cholestasis in the Perfused Rat Liver and Its Reversal by Tauroursodeoxycholate: An Ultrastructural Study", Proc. Soc. Exp. Biol. and Med., vol. 199, pp. 54–58, 1992.

S. Kanai et al., "Effect of tauroursodeoxycholate on the biliary transport maximum of sulfobromophthalein in the rat", Jour. Lab. Clin. Med., vol. 108, pp. 601–607, 1986.

R. Coleman, "Bile salts and biliary lipids", Biochem. Soc. Transactions, vol. 15, pp. 68S–80S, 1987.

Guentert et al., "Accelerated Elimination of Tenoxicam and Piroxicam by Cholestryamine", Abstracts of Papers, vol. 43, No. 2, p. 179.

M. Nakagawa et al., "Comprehensive Study of the Biliary Bile Acid Composition of Patients with Cystic Fibrosis and Assoc. Liver Disease before and after UDCA Admin.", Hepatology, vol. 12, No. 2, pp. 322–334, 1990.

M.A. Al–Meshal et al., "Interruption of the enterohepatic circulation on indomethacin by cholestyramine in rabbits", Intl. Jour. of Pharmaceutics, vol. 64, pp. 155–160, 1990.

J. Cotting et al., "Effects of ursodeoxycholic acid treatment on nutrition and liver function in patients with cystic fibrosis and longstanding cholestasis", Gut, vol. 31, pp. 918–921, 1990.

B. Kallinowski et al., "Effective Treatment of Cyclosporine–Induced Cholestasis in Heart–Transplanted Patients Treated with Ursodeoxycholic Acid", Transplantation, vol. 51, No. 5, pp. 1128–1129, 1991.

R.L. Smith "Excretion of Drugs in Bile", *Handbook of Experimental Pharmacology*, vol. 28, part 1, pp. 354–389, 1971.

R.O. Day et al., "Clinical Pharmacology of Non–Steroidal Anti–Inflammatory Drugs", Pharmac. Ther., vol. 33, pp. 383–433, 1987.

S.K. Cole et al., "Targeting drugs to the enterohepatic circulation: A potential drug delivery system designed to enhance the bioavailability of indomethacin", Intl. Jour. Pharmaceutics, vol. 80, pp. 63–73, 1992.

C. Benveniste et al., "Indirect assessment of the enterohepatic recirculation of piroxicam and tenoxicam", Eur. Jour. Clin. Pharmacol., vol. 38, pp. 547–549, 1990.

A. Hofmann, "Targeting Drugs to the Enterohepatic Circulation: Lessons from Bile Acids and Other Endobiotics", Jour. of Controlled Release, vol. 2, pp. 3–11, 1985.

H.T. Schneider et al., "Biliary elimination of non–steroidal anti–inflammatory drugs in patients", Br. Jour. Clin. Pharmac., vol. 29, pp. 127–131, 1990.

J.H. Lewis, "Hepatic toxicity of nonsteroidal anti–inflammatory drugs", Clinical Pharmacy, vol. 3, pp. 128–137, 1984.

S. Hatono et al., "Absorption, Biliary Excretion, and Metabolism of a New Cholelitholytic Agent, Ursodeoxycholyl N–Carboxymethylglycine and Its Esters in Rats", Jour. Pharmacobio–Dyn., vol. 14, pp. 561–566, 1991.

C.P. Siegers et al., "Biliary excretion and enterohepatic circulation of paracetamol in the rat", Xenobiotica, vol. 13, No. 10, pp. 591–596, 1983.

Y. Delage et al., "Influence of dehydrocholate and taurocolate on bromsulphthalein uptake, storage, and excretion in the dog", Gut, vol. 16, pp. 105–108, 1975.

Tokyo Cooperative Gallstone Study Group, "Efficacy and Indications of Ursodeoxycholic Acid Treatment for Dissolving Gallstones", Gastroenterology, vol. 78, pp. 542–548, 1980.

D.M. Heuman et al., "Conjugates of Ursodeoxycholate Protect Against Cytotoxicity of More Hydrophobic Bile Salts: In Vitro Studies in Rat Hepatocytes and Human Erythrocytes", Hepatology, vol. 14, pp. 920–925, 1991.

S. Mandiola et al., "Biliary excretion of ampicillin in the anesthetized dog.", Surgery, vol. 71, No. 5, pp. 664–674, 1972.

R.J. Vonk et al., "The Influence of Taurocholate and Dehydrocholate Choleresis on Plasma Disappearance and Biliary Excretion of Indocyanine Green in the Rat", Naunyn–Schm. Arch. Pharm., vol. 282, pp. 401–410, 1974.

R.N. Berk et al., "The Role of Bile Salts in the Hepatic Excretion of Iopanoic Acid", Investigative Radiology, vol. 9, pp. 7–15, 1974.

G.L. Plaa, "The Enterohepatic Circulation", *Handbook of Experimental Pharmacology*, vol. 28, part 3, pp. 130–149, 1975.

I.A.D. Bouchier, "The Medical Treatment of Gallstones", Ann. Rev. Med., vol. 31, pp. 59–77, 1980.

PHARMACEUTICAL COMPOSITION CONTAINING A LOW DETERGENT EFFECT BILE SALT AND AN ACTIVE COMPOUND THAT UNDERGOES BILIARY EXCRETION AND/OR ENTEROHEPATIC RECYCLING

This invention relates to pharmaceutical compositions. In preferred embodiments, the invention relates to pharmaceutical compositions of drugs which undergo biliary excretion and/or enterohepatic recycling. The invention also relates to a method of formulating a pharmaceutically active agent into a pharmaceutical composition and to a method of administering drugs, as well as to the use of drugs and certain other ingredients in the preparation of pharmaceutically useful compositions. The invention also provides a means of avoiding hepatic and gastrointestinal toxicity due to drug administration.

It is in general known to formulate surfactants with pharmaceutical agents for the purpose of solubilizing them as in, for example, EP-A-0179583 and WO-A-9012583. EP-A-0274870 teaches that non-steroidal anti-inflammatory drugs (NSAIDs), which are in general poorly water soluble, can be administered, as well as solubilized, as micelles and that this has advantages of (a) potentially protecting the drug from the acidic and enzymatic environment of the stomach and (b) protecting the gastrointestinal mucosa from adverse effects of the drug (such as gastrointestinal bleeding, which is induced by NSAIDs including aspirin, indomethacin and piroxicam). Bile acids (or bile salts—the exact nature and proportion of the species present will depend on the pH of the environment and so the terms are used interchangeably in this specification) are naturally occurring surractants. They are a group of compounds with a common "backbone" structure based on cholanic acid found in all mammals and higher vertebrates. The detergent properties of bile acids are largely determined by the number and orientation of hydroxyl groups substituted onto a steroidal nucleus. Bile acids may be mono-, di- or tri-hydroxylated; they always contain a 3-α hydroxyl group, whereas the other hydroxyl groups, most commonly found at $C_6$, $C_7$ or $C_{12}$, may be positioned above (β) or below (α) the plane of the molecule. Many permutations of hydroxyl configuration are possible, but certain configurations are very much more common in nature than others. In most animal species there is a recognised pattern to the usual composition of the bile acids found in the bile acid pool of individual animals.

Bile acids are synthesized in vivo from cholesterol in the liver by hydroxylation and other modifications. Virtually all bile acids found in the bile of mammals and higher vertebrates are amidated at the $C_{24}$ position with either taurine or glycine. The extent to which various bile acids are amidated with either glycine or taurine shows considerable variation between species and depends on the availability of taurine as a substrate for the conjugating enzyme. The term "bile acids" as used herein includes such amidated moieties.

In its role as an exocrine gland the liver secretes bile, a solution of detergent bile acids, which may be stored and further concentrated by the gall-bladder between meals. Following gall-bladder contraction in response to the gastrointestinal hormone cholecystokinin, when food is consumed, the bile acids enter the duodenum where they perform their major role as surfactants: they function to enhance the digestion and absorption of dietary lipids and lipid soluble vitamins. Bile acids also increase the action of pancreatic lipases. After completing their role in digestion bile acids are avidly conserved by the body: they are efficiently reabsorbed by an active receptor mediated process from the terminal ileum and returned to the lever, via the hepatic portal vein, and undergo further receptor enhanced extraction prior to resecretion into the bile. Thus the almost continuous flow of bile acids is topographically localized and limited to the liver, biliary tree, intestine, enterocytes and hepatic portal venous system, and thus comprises the enterohepatic circulation. The enterohepatic circulation functions not only to conserve valuable detergent bile acid molecules, by allowing their many times repeated use, but also allows bile acids to maintain continuous homeostatic control over a variety of metabolic events. Bile acids have an essential role in regulating the synthesis and transport of a variety of lipids within and between the cells, tissues and organs which encounter the bile acids during their enterohepatic circulation.

In addition to bile acids, many drugs and drug metabolites are also secreted into the bile. The extent to which drug molecules are secreted into the bile is dependent upon their physical-chemical characteristics and molecular weight. Generally drugs which have a molecular weight above the biliary threshold (typically about 300 kDa in man) and have tendency to be anionic at physiological pH are excreted in the bile. The extent to which a drug is then reabsorbed intact from the gastrointestinal tract depends both on its chemical stabilty in the bile and gastrointestinal milieu and on its absorption characteristics.

Many drugs undergo enterohepatic recycling detailed reviews of drugs undergoing biliary excretion and enterohepatic circulation have appeared, R. L. Smith (1971) in *Handbook of Experimental Pharmacology* (B. B. Brodie & J. R. Gillette, eds.) Vol. 28, Part 1 pp. 354–389 and also G. L. Plaa (1975) in *Handbook of Experimental Pharmacology* (J. R. Gillette and J. R. Mitchell, eds.) Vol. 28, Part 3 pp. 130–149.

A category of drugs which is particularly affected by biliary excretion are the non-steroidal anti-inflammatory drugs, exemplified by indomethacin. Indomethacin is used in the treatment of both acute and chronic inflammatory states (R. O. Day et al (1987) *Pharmacol. Ther*. 33, 383–433). Indomethacin has a low plasma clearance, short plasma half-life, a low volume distribution (K. Kwan et al (1975) *J. Pharmacokinetics & Biopharmaceutics* 4, 255–280) and is mainly excreted via the hepato-biliary route (H. B. Hucker et al (1966) *Pharmacol. Exp. Ther*. 153, 237–249). Extensive clearance of intact indomethacin into the bile has been shown to result in its enterohepatic circulation and is believed to be responsible for the wide inter-subject dose response observed with this drug (D. E. Duggan et al (1975) *Biochem. Pharmacol*. 25, 1749–1754). This phenomenon has also been shown to occur with other non-steroidal anti-inflammatory drugs such as paracetamol, ibuprofen, sulindac, tenoxicam and piroxicam.

S. K. Cole et al ((1992) *Int. J. Pharmaceutics* 80, 63–73) suggested that the inter-subject variation in indomethacin (and other enterohepatic recycled drugs) bioavailability was due to the wide inter-subject variation in individual bile acid pool-size and composition. This hypothesis was based on (i) the observation that exogenously added bile acids increased the bioavailability of indomethacin, while decreasing inter-subject variation (ii) previous reports that exogenously added bile acids increased the biliary excretion of other organic anions such as ampicillin, (S. Mandiola et al (1972) *Surgery* 71, 664–674) iopanoic acid (R. N. Berk et al (1974) *Invest. Radiol*. 9, 7–15), indocyamine green (R. Vonk et al (1974) *Naunyn Schmiedeberg's Arch*. 282, 401–410), bromosulphthalein (Y. Delage et al (1975) *Gut* 16, 105–108) and bilirubin (A. Esterller et al (1988) *O.J. Exp. Physiol*. 69, 217–225), in a variety of animal species; and (iii) interruption of the enterohepatic circulation with bile acid sequestrants, such as activated charcoal or cholestyramine, decreased the bioavailability of orally administered drugs which undergo enterohepatic recycling (M. A. Al-Meshal et al (1990) *Int. J. Pharm.* 64, 155–160; B. Dordoni et al (1973) *Br. Med. J.* 14, 86–87; C. P. Siegers et al (1983) *Xenobiotica* 13, 591–596; T. W. Guentert et al (1988) *Clin. Pharmacol. Ther.* 43, 179; C. Benveniste et al (1990) *Eur. J. Clin. Pharmacol.* 38, 547–549). Removal of bile acids from the enterohepatic circulation would essentially remove one of the major driving forces for the generation of bile flow.

Previous studies have suggested that sodium deoxycholate and sodium cholate enhance the dissolution of indomethacin and phenylbutazone in pH 7.3 buffer, at 37° C., by the formation of mixed micelles (S. Miyazaki et al (1973) *Chem. Pharm. Bull.* 27, 2468–72). The absence of bile acid mixed micelles to solubilize these drugs was proposed as the explanation for the reduced indomethacin levels in the plasma of rats undergoing biliary drainage, (S. Miyazaki et al (1980) *Chem. Pharm. Bull*, 28, 323–326). Interestingly, in patients undergoing biliary drainage, a situation in which the levels of bile acids in bile and therefore the enterohepatic circulation of drugs are substantially reduced, only relatively low levels of non-steroidal anti-inflammatory drugs were found in the bile (H. T. Schneider et al (1990) *Br. J. Clin. Pharmacol.* 29, 127–131). The lower than expected levels of non-steroidal anti-inflammatory drugs found in the bile of patients undergoing biliary drainage, further suggests the importance of bile acids in promoting enterohepatic recycling. S. K. Cole et al ((1992) *Int. J. Pharm*. 80, 63–73) demonstrated an enhanced in vitro dissolution of indomethacin in the presence of bile acids. This enhanced solubilisation did not translate into an enhanced absorption rate in vivo, however. As discussed above, the human bile acid pool size is subject to wide inter-subject variation, one possible consequence of which is the formation of cholesterol gallstones. Cholesterol gallstones may be dissolved by expanding the bile acid pool with exogenously added bile acids, usually chenodeoxycholate or ursodeoxycholate, resulting in a decrease in inter-subject variation in both bile acid pool size and composition (A. F. Hofmann (1985) *J. Controlled Release* 2, 3–11; A. F. Hofmann (1988) in: *The Liver: Biology and Pathobiology* (Arias I. M., Jakoby, W. G., Popper, H., Schachter, D. and Shafritz, D. A. eds.) 2nd Edition, Raven, N.Y., pp. 552–572).

The art has therefore suggested the use of surfactants in formulating drugs such as NSAIDs and the use of bile acids in such situations. However, there is a problem if this teaching is followed. Many bile acids, particularly some of the dihydroxy bile acids, may on their own in certain individuals result in adverse effects on the liver, such as during the dissolution of gallstones with chenodeoxychoiate. Furthermore, certain bile acids in combination with non-steroidal anti-inflammatory drugs may increase the toxic load on all the tissues exposed to their enterohepatic recycling, resulting in substantial cell erosion in the gastrointestinal tract and/or enhanced hepatic toxicity. Their use is therefore contraindicated. However, it has now been realised that certain bile acids which exhibit a peculiarly low detergent effect can be used as formulatory excipients for pharmaceutically active agents; the use of such bile acids retains many of the advantages of the use of bile acids without some or all of the attendant disadvantages. Further, by administering in combination with a pharmaceutically active agent a quantity of a low detergent bile acid, the composition and size of the endogenous bile acid pool can be standardised, at least to a degree: more reliable drug delivery can result from more predictable biliary excretion and enterohepatic recycling of the pharmaceutically active agent.

According to a first aspect of the invention, there is provided a pharmaceutical composition comprising a pharmaceutically active compound and a bile acid having a low detergent effect.

The present invention makes possible the oral administration of a wide variety of compounds which, because of problems with enterohepatic recycling and/or biliary excretion, would otherwise have to be administered by a parenteral route.

A wide range of pharmaceutically active compounds can be formulated by means of the invention. Generally, the invention is applicable to compounds capable of being administered orally (at least when formulated by means of the invention if not otherwise). The present invention can therefore be used to formulate practically any orally active pharmaceutically active agent conveniently and relatively inexpensively, especially those (a) which need to be protected from the acidic and enzymatic environment of the stomach and (b) for which the gastrointestinal mucosa should be protected from adverse effects of the drug.

The invention finds particular applications in formulating those pharmaceutically active agents which undergo substantial biliary excretion and/or enterohepatic recycling. As has previously been mentioned, drugs which have a molecular weight of over 300 kDa exceed the biliary threshold in man, and drugs which tend to be anionic at physiological pH, tend to be excreted in the bile; but these properties are only of general guidance to the behaviour of the drug in relation to bile and not necessarily predictive. More generally, drugs which have significant hepatocyte receptor binding capability will as a rule be significantly excreted in the bile and/or subject the enterohepatic recycling.

The above comments provide the basis for selecting drugs whose oral administration can markedly benefit from the invention, as a number of practical tests can readily be devised for the purpose.

First, and preferably, pharmaceutically active compounds which are candidates for formulation by the invention may be Identified in an isolated perfused rat liver model.

The isolated rat liver includes the biliary system. A suitable model is described in Barnwell et al (1983) *Biochem J*. 216 107–111and can readily be adapted for the present purposes. Essentially, the candidate active compound is formulated into the aqueous) perfusion medium. Clearance of the compound into the bile is then determined. This can simply be achieved by collecting the bile and using an assay appropriate for the compound in question. In the continuous perfusion model described in Barnwell et al, a significant amount of bile clearance may be said to be represented by at least 5% (w/w) of the administered drug appearing in the bile over 5 to 6 hours. In some circumstances, substantially more than 5% may appear in the bile over this time period: at lest is 10%, 25%, 50%, 75% or even 90% may appear. Although the perfusion medium is aqueous, and is therefore ideally suited for assessing water-soluble compounds, insoluble compounds can also be assessed. Those skilled in the art will be aware of the many techniques available for dealing with water-insoluble drugs under such circumstances: for example, a water-insoluble drug may be pre-dissolved in a solvent (such as DMSO or ethanol), and the resulting solution added to the perfusion medium; or the drug may be adsorbed onto a soluble carrier molecule, which may be a protein such as albumin. Other perfusion models (for example single pass as opposed to continuous systems) can readily be devised.

Secondly, instead of the above ex vivo model, an in vivo system could be used. For example, the bile duct of a rat may be cannulated, so that bile may be collected. The candidate compound is administered orally to the rat and subsequently assayed in the bile as described above.

Thirdly, an in vitro model may be used, based for example on binding of the compound under test to isolated hepatocytes. The isolated hepatocyte system of Miyazaki et al (1984) *Dig. Dis. and Sci.* 29 1123–1130 may be used, with appropriate modifications.

Further examples of drugs which undergo substantial biliary excretion and/or enterohepatic recycling are antibiotics of the penicillin type, eg ampicillin, amoxycillin, aziocillin, benzylpenicillin, cloxacillin and also many cephalosporins. Other antimicrobials which may benefit from improved enterohepatic delivery include doxycycline, tetracycline, cefoperazone, chloramphenicol and cefoxitin. Many other groups of drugs may also benefit from predictable enterohepatic recycling and therefore improved reliability, these include: cardiovascular agents (such as prazosin, reserpine and digoxin), immunomodulators/antineoplastic agents (such as cyclosporin, methotrexate, tamoxifen, vincristine and vinblastine), sex hormones (such as clomiphene and oestrogens), xanthines (such as theophylline), antimycobacterial agents (such as clofazimine and rifampicin), vasoldilators (such as dipyridamole), antimalarials (such as chloroquine), antimuscarihic agents (such as propantheline), antiepileptics (such as phenytoin) and antigout agents (such as colchicine). Another group of compounds of interest used as major tranquillisers include haloperidol, chlorpromazine and perphenazine. These compounds are of particular interest because they not only undergo erratic enterohepatic recycling and cause adverse liver effects, but also have high hepatic first-pass metabolism. These pharmacokinetic and toxicological implications may result in the combination of the present invention together with the liver by-pass technology described In WO-A-9206680. These compounds also have a very short plasma half-life therefore benefiting from the sustained-release delivery described in WO-A-9206680.

The invention may also be used to formulate non-steroidal anti-inflammatory drugs (NSAIDs); there are some of them which can be formulated particularly satisfactorily by means of the present invention. These are: indomethacin, paracetamol, ibuprofen, sulindac, tenoxicam and piroxicam.

Bile acids vary greatly in their individual detergent strength. Generally dihydroxy bile acids such as chenodeoxycholate and deoxycholate are stronger detergents than trihydroxy bile acids such as cholic acid. This to some extent may be demonstrated by the characteristic of critical micellar concentration (CMC), in a measure of self association in aqueous solution using techniques such as incorporation of fluorescent dyes or spin label probes into the hydrophobic interior of the bile acid micelles. For reviews of this area see R. Coleman (1987) *Biochem. Soc. Trans.* 15 685–805 and M. C. Carey (1985) in: "Sterols and Bile Acids" (Danielsson, H. and Sjovall, J. eds.), Elsevier, Amsterdam, pp. 345–402. Generally dihydroxy bile acids have a CMC in the range of 1–3 mM while trihydroxy bile acids have a CMC in the range of 5–10 mM. A very good model for testing the detergent strength of bile acids is the human (or other species) erythrocyte. Detergent bile acids initially solubilize lipids and surface associated proteins, such as acetylcholinesterase from erythrocytes without causing cell lysis as measured by the leakage of haemoglobin into the isotonic incubation solution. Substantial erythrocyte lysis with dihydroxy bile acids occurs in the 1–5 mM concentration range and in the 20–30 mM range for trihydroxy bile acids. An exception to this trend is the dihydroxy bile acid ursodeoxycholate which despite demonstrating the powerful self-association characteristics of a dihydroxy bile acid, with a CMC in the 1–3 mM range, has no measurable ability to lyse red blood cells even at concentrations in excess of 60 mM (R. Coleman (1987) *Bichem. Soc. Transactions* 15, 68 S–80 S; D. M. Heuman et al (1991) *Hepatology* 14, 920–926). This lack of detergent effect of ursodeoxycholate on biological systems has also been observed in the isolated perfused rat liver fitted with a bile duct cannula (S. G. Barnwell et al (1983) *Biochem. J.* 216, 107–111) and in isolated human hepatocytes K. Miyazaki et al (1984) *Dig. Dis. and Sci.* 29, 1123–1130. The low detergent capacity of ursodeoxycholate is probably also reflected in the decreased incidence of gastrointestinal side-effects and lower hepatic intracellar enzyme levels measured in the plasma of subjects receiving ursodeoxycholate, rather than chenodeoxycholate, as their gallstone dissolution therapy (I. A. D. Bouchier (1980) *Anna. Rev. Med.* 31, 59–77 and Tokyo Co-operative Gallstone Study Group (1980) *Gastroenterology* 78, 542–548).

The human erythrocyte lysis test can be used as the basis for identifying bile acids which are useful in the present invention. In general, a bile acid which does not significantly lyse erythrocytes at a concentration of at least 30 mM may be used. Preferably, significant lysis will not take place below 40 mM, 50 mM or even 60 mM. Ursodeoxycholate, whose non-amidated structure is:

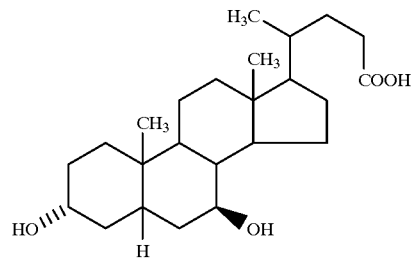

preferred for use in the invention. Ursodeoxycholate is readily available from Thames Laboratories Ltd, Wrexham, UK, by whom it is sold under the trademark URSOFALK for gallstone dissolution. It may also be obtained from Alfa Chemicals Limited, UK, or Erregierre Industria Chimica SpA, Italy.

The use of ursodeoxycholate to alter the endogenous bile acid pool to facilitate the delivery of drugs could take a number of forms. Ursodeoxycholate may be administered as an acid or a salt eg sodium salt. Bile acids in vivo exist as conjugates, usually with the amino acids glycine or taurine. Furthermore, ursodeoxycholate is not the only poor-detergent bile acid which could be used as an aid to drug delivery. Other examples include ursodeoxycholyl N-carboxymethylglycine and its esters (S. Hatano et al (1991) *J. Pharmacobio-Dyn.* 14, 561–566), the short side chain bile acids norcholic and norursocholic acid (J. Lillienau et al (1991) *Am. J. Physiol.* 261, G1057–G1064), β-muricholic acid (S. Kanai et al (1990) *Life Sciences* 47, 2421–2428), 7-keto-lithocholate and taurodehydrocholate. However, many of these examples of non-membrane damaging bile acids do not become major components of the enterohepatic circulation in the same way as ursodeoxycholate, which is therefore preferred. The important criteria for selecting a bile acid as a drug delivery aid is that it should not be membrane damaging, as defined in the red blood cell lysis test discussed earlier, and should persist in a non-membrane damaging form, either in its original form or as a non-membrane damaging metabolite, within the enterohepatic circulation. It should be noted that to assess a bile acid using the red cell lysis test the sodium salt or amino acid conjugate may have to be used to ensure solubility in isotonic saline at neutral pH.

Of further note is the ability of poor-detergent bile acids to prevent the toxicological effects of more detergent bile acids. For example ursodeoxycholate reduces the biliary excretion of membrane enzymes in rats induced by more detergent dihydroxy and trihydroxy bile acids (K. Kitani et al (1985) *Am. J. Physiol.* 248, G407–G417 and in human erythrocytes and mono-layer cultures of isolated rat hepatocytes (D. M. Heuman et al (1991) *Hepatology* 14, 920–926. These studies have been extended to a clinical environment in which ursodeoxycholate has been shown to reverse measures of hepatic damage in patients with chronic active hepatitis (E. Rolandi et al (1991) *Eur. J. Clin. Pharmacol.* 40, 473–476), primary biliary cirrhosis (R. E. Poupon et al (1991) *New England Journal of Medicine* 324, 1548–1554) and cystic fibrosis (J. Cotting et al (1990) Gut 33, 918–921; M. Nakagawa et al (1990) *Hepatology* 12, 322–334).

Many drugs are known to cause adverse effects upon the liver resulting in liver damage and cholestasis (J. Reichen and F. R. Simon (1988) in: "The Liver: Biology and Pathobiology", 2nd Edition (I. M. Arias, W. B. Jakoby, H. Popper, D. Schacter and D. A. Shafritz, eds.), Raven Press Ltd, New York, pp. 1105–1123). Ursodeoxycholate has been shown to reverse drug-induced cholestasis, in the isolated perfused rat liver, caused by estradiol-17-β-D-glucaronide and chlorpromiazine (C. O. Abernathy et al (1992) *Proc. Soc. Exp. Biol. and Med.* 199, 54–58). Cyclosporine, an immunosuppressive drug used in the management of transplant patients, often causes the onset of cholestasis. In heart transplant patients with cyclosporine-induced cholestasis, ursodeoxycholate has been found to reverse the elevated plasma levels of liver enzymes and bilirubin (B. Kallinowski et al (1991) *Transplantation* 51, 1128–1129. Interestingly, the non-steroidal anti-inflammatory drugs as a group commonly give rise to hepato-toxic events (J. H. Lewis (1984) *Clinical Pharmacy* 3, 128–137) confirming that the use of ursodeoxycholate as a drug delivery aid may have toxicological as well as pharmacokinetic advantages resulting from the replacement of the bile acid pool with less membrane-damaging bile acids.

In summary, the invention can result in: enhanced bioavailability of these drugs, by increasing enterohepatic recycling; modification of the extent of biliary excretion, thereby achieving a more reproducible dose response and therefore a reduced inter-subject variation; replacement of the bile acid pool with less toxic bile acids, which reduces the risk of drug and bile acid-induced toxicity in the liver and gastrointestinal tract.

The absolute and relative amounts of the pharmaceutically active substance and bile acid will depend on the pharmacological and physico-chemical properties of both. As general guidance, though, the weight ratio of pharmaceutically active substance to bile acid may range from 0.5:1 to 100:1, with from 1:1 to 10:1 being typical and a ratio of about 3:1 often being used in practice. The amount of pharmaceutically active substance in each dose of a composition of the invention may range widely, for example from 250 $\mu$g to 1g; the amount of bile acid present will usually vary within somewhat narrower limits, for example from 50 mg to 500 mg, and typically from 100 mg to 300 mg.

Other excipients may be present. For example plasticisers and/or binding agents may be used when coating seed crystals or other matrix materials. Suitable plasticisers include polyvinyl pyrrolidone (povidone), hydroxypropyl methyl cellulose (HPMC), propylene glycol, polyethylene glycol or hydroxypropyl cellulose. Some of these materials can function as additional solubilising agents, and the presence of these or other solubilising agents is also within the scope of the invention. Lecithin is a suitable lipid solubilising agent, as are its naturally occurring breakdown products, lysolecithin and free fatty acids. In the case where stabilisation of the enterohepatic circulation (eg haloperidol) together with liver by-pass is required the formulation may also contain a substantial amount of oleic acid. Furthermore, if a sustained release preparation is required, GELUCIRES® may also be used as described in WO-A-9206680. Alternatively or in addition to these components various antioxidants and preservatives may also be included in the formulation.

The formulation approach described in WO-A-9206680 may be particularly appropriate to combine with that of the present invention when the active substance is prone to significant hepatic first pass metabolism, such as haloperidol, chlorpromazine and perphenazine, as has briefly been described above. WO-A-9206680, the contents of which are herein incorporated by reference to the extent that the law allows, relates to a pharmaceutical formulation comprising:

(a) a $C_{12}$–$C_{24}$ fatty acid (such as linoleic or, preferably, oleic acid); and (b) a pharmaceutically active substance;

wherein a portion of the $C_{12}$–$C_{24}$ fatty acid is formulated for non-sustained release on non-parenteral administration and wherein a portion of the $C_{12}$–$C_{24}$ fatty acid and at least a portion of the pharmaceutically active substance are formulated for sustained release on non-parenteral administration.

Compositions in accordance with the invention can in principle be prepared simply by mixing the ingredients together. According to a second aspect of the invention, therefore, there is provided a process for the preparation of a composition as described above, the process comprising admixing the ingredients together.

It is preferred for the pharmaceutically active agent and the bile acid to be intimately admixed. While this may be achieved mechanically, for example in a ball mill, in practice it is found that evaporation from a common solvent often yields a more homogeneous result. The nature of the common solvent will of course depend on the solubility properties of the ingredients (particularly the pharmaceutically active agent); lower alcohols (such as $C_{1-3}$ alcohols, particularly methanol, may be preferred, as may other volatile organic solvents.

The bile acid and pharmaceutically active agent composition of the invention may be formulated as either a solid or a liquid and may be coated onto carrier particles if required. Suitable carrier particles include, but are not limited to, sucrose. The composition, whether or not coated onto carrier particles, may be filled into capsules or tabletted if required. Hard or soft gelatin capsules may be used although hard gelatin capsules may be preferred.

Solid formulations include powders, granules and tablets and may contain various excipients. Tablet and granular formulations may contain binding agents such as starch, gelatin, acacia or, especially, polyvinylpyrrolidone in an amount of from 1 to 15%, preferably 1 to 5% by weight. For granular formulations, an amount of about 3% by weight of polyvinylpyrollidone has been found to give particularly satisfactory powder binding characteristics.

Disintegrating agents may also be present and these include polymers such as corn starch and alginic acid. Disintegrating agents which have been found to be particularly suitable include cross linked polymers, typically polymers of sodium carboxymethylcellulose such as croscarmellose sodium. The disintegrating agent will generally be present in amount of from 1 to 15%, preferably from 1 to 5% and, for granular preparations, more preferably about 3% by weight of the formulation.

In addition, a filler or diluent may be included in the formulation to enable a suitable dosage size to be achieved. Fillers and diluents are well known to those skilled in the art of formulation chemistry and include calcium carbonate, sodium carbonate, lactose, calcium phosphate and sodium phosphate. In the present invention, however, lactose has been found to be particularly suitable. The filler or diluent will generally be present in an amount of from 20 to 80%, typically from 30 to 60%. If the formulation is in the form of capsules it is important to be able to achieve accurate and consistent capsule filling and for this, an amount of from 45 to 55%, especially about 47% of filler has been found to be appropriate.

The formulation of the invention may be enteric coated in order to delay release of the pharmaceutically active compound until the formulation reaches the ileum. This may be either to prevent the active compound from being broken down in the acidic environment of the stomach or to prevent the active substance from attacking the gastric mucosa. The latter reason is particularly important in the case of NSAIDs such as indomethacin. In addition, the localised pH of the ileum is such that it will generally permit much more rapid dissolution of the pharmaceutically active substance and the bile acid than if they were released in the stomach.

Enteric coating substances are well known to those skilled in the art but methacrylic acid copolymers have been found to be particularly suitable. An example of such a methacrylic acid coating copolymer is EUDRAGIT L100™ (Rohm Pharma, Germany).

When the enteric coating is applied to capsules, additional formulation aids may be used and these include plasticisers such as diacetylated monoglyceride and anti-adhering agents such as talcum.

The coating materials may be applied by conventional means, for example by forming a suspension in a suitable solvent or combination of solvents and spray coating onto the formulation.

Administration of the compositions of the invention will generally be under the guidance of the physician, clinician or veterinarian. As such a wide range of pharmaceutically active substances can be formulated by means of the invention, it is clearly not appropriate for dosage recommendations to be given here. As to the route of administration, formulations in accordance with the invention will generally be for oral administration.

According to a third aspect of the invention, there is provided the use of a pharmaceutically active agent useful in a medical condition and a bile acid having a low detergent effect in the manufacture of a medicament for treating, preventing or managing the medical condition.

The invention can be used in a method of treating, preventing or managing a medical condition, the method comprising administering to a subject a pharmaceutical composition as described above.

Preferred features of the second and subsequent aspects of the invention are as for the first aspect mutatis mutandis.

The invention will now be illustrated by the following examples. The examples refer to the accompanying drawing, in which:

FIG. 1 compares the targeting efficiency of bile acid/indomethacin formulations with INDOCID™. In particular, the graph shows the relationship between the in ratio of the indomethacin AUC with the bile acid/indomethacin formulation to the AUC for INDOCID™, against the ln of AUC ($\mu$g.ml.h$^{-1}$) indomethacin from INDOCID™ for 10 subjects.

EXAMPLE 1

Preparation of Enteric Capsules

A wet granulation process was used to form an intimate mixture of the following ingredients:

| Material | % w/w | amount (g) |
|---|---|---|
| Indomethacin (micronised) | 15.63 | 46.88 |
| Ursodeoxycholic acid (micronised) | 31.25 | 93.75 |
| Lactose | 47.12 | 141.37 |
| Croscarmellose sodium | 3.00 | 9.00 |
| Povidone | 3.00 | 9.00 |
| Total | 100.00 | 300.00 |

The ingredients were mixed thoroughly before being screened though a 1.0 mm aperture sieve screen. 90 cm$^3$ of a 10% w/v aqueous solution of polyvinyl pyrrolidone sold under the trade mark POVIDONE™ was prepared by addition of the POVIDONE™ to purified water with stirring. The POVIDONE™ solution was then added slowly to the screened dry mix and mixed until a suitable wet mass was obtained. The wet mass was then screened through a 1.7 mm sieve screen and the resultant mass transferred to a UNI-GLATT™ fluidised bed spray drier and dried at 60° C. until a moisture content of less than 2% w/w was obtained. The dried mass was then screened through a 1.0 mm aperture sieve screen and then filled to a fill weight of 320 g into size 0 hard gelatin capsules which were then gelatin banded.

Following the preparation of the capsules as described above, the capsules were then enteric coated using the following coating components.

| Material | % w/w | mg/capsule (approx) |
|---|---|---|
| Methacrylic acid copolymer | 65.0 | 25.0 |
| Diacetylated monoglycerides | 10.0 | 3.8 |
| Talcum | 25.0 | 9.6 |
| Total | 100.0 | 38.4 |

The enteric film forming material was methacrylic acid copolymer EUDRAGIT L100™ (Rohm Pharma, Germany). Diacetylated monoglyceride (a plasticiser) and talcum (an anti-adhering agent) were also included as formulation aids. The coating materials were applied as a water/ethanol suspension using a commercial fluidised-bed spray coating procedure carried out by Pharma-Vinci A/S, Denmark.

EXAMPLE 2

10.0 g of ursodeoxycholate (sodium salt) was dissolved in 100.0 g of methanol and heated with stirring under reflux for 10 minutes before adding 2.5 g of indomethacin. After dissolving the indomethacin the solution was evaporated in an EVAPOTEC® rotary film evaporator, the water bath temperature being approximately 50° C. and a strong vacuum maintained throughout. The resulting product crystals were recovered and found to dissolve in pH 6.8 phosphate buffer.

EXAMPLE 3

The procedure outlined in Example 2 was used, except with the following ingredients:

| | |
|---|---|
| Ursodeoxycholate | 10.0 g |
| Methanol | 100.0 g |
| Diclofenac | 2.5 g |

EXAMPLE 4

The procedure outlined in Example 2 was used except with the following ingredients:

| | |
|---|---|
| Ursodeoxycholate | 10.0 g |
| Methanol | 100.0 g |
| Naproxen | 2.5 g |

EXAMPLE 5

The procedure outlined in Example 2 was used except with the following ingredients:

| | |
|---|---|
| Ursodeoxycholate | 10.0 g |
| Methanol | 100.0 g |
| Ibuprofen | 2.5 g |

EXAMPLE 6

Dissolution Studies

In order to evaluate the dissolution behaviour of formulations according to the present invention in comparison to other similar formulations, a test method was devised based on the USP XXII dissolution test for tablets and capsules. The aim of the test was to subject the samples to an environment similar to that in the intestine.

The dissolution apparatus used was as specified by the USP XXII (apparatus 2) and the dissolution medium consisted of a 1 in 5 dilution of either pH 6.4 phosphate buffer in distilled water or pH 7.2 phosphate buffer in distilled water, equilibrated to 37° C. for indomethacin and ursodeoxycholic acid tests respectively. A volume of 750 cm$^3$ was added to each dissolution vessel with a paddle rotation speed of 100 rpm. The capsules were dropped into each of the dissolution vessels with a wire sinker around the body of each capsule. At each time point a 5 cm$^3$ aliquot of the dissolution medium was removed and replaced with a 5cm$^3$ aliquot of fresh dissolution medium. The samples were centrifuged to remove any suspended undissolved material and then analysed for both their indomethacin and ursodeoxycholic acid content. Indomethacin was determined by HPLC using a reference standard. Ursodeoxycholic acid was determined using a bile acid enzymatic assay kit (Sigma Chemicals Ltd) against a standard calibration curve. The results are presented in Table 1.

TABLE 1

| Time (mins) | # Indomethacin Release | % Urosdeoxycholate Release |
|---|---|---|
| 0 | 0 | 0 |
| 15 | 93.8 | 97.9 |
| 30 | 95.8 | 100.7 |
| 45 | 95.8 | 101.2 |
| 60 | 95.4 | 101.2 |

The results show that the formulation of Example 1 achieves a rapid dissolution of both indomethacin and ursodeoxycholic acid. This is a clear demonstration that, using the formulations of the present invention, it is possible to achieve effective delivery of both the active substance and the bile acid to the small intestine.

COMPARATIVE EXAMPLE

In order to demonstrate the effectiveness of the formulation of Example 1, the dissolution was compared with various other commercially available preparations containing ursodeoxycholic acid. Because there are available no matched preparations containing both indomethacin and ursodeoxycholic acid, preparations containing only ursodeoxycholic acid were evaluated. Dissolution test parameters were as described in Example 6 but the volume of dissolution medium was adjusted so as to obtain a matched concentration of ursodeoxycholic acid to that obtained for the formulation of Example 1. The commercially available preparations which were used are listed below.

URSOFALK™ (250 mg ursodeoxycriolic acid) capsules—Thames Laboratories Limited (U.K.)

DESTOLIT™ (150 mg ursodeoxycholic acid) tablets—Marion Merrell Dow (U.K.)

ACTIGALL™ (250 mg ursodeoxycholic acid) capsules—Ciba Pharmaceutical Co. (U.S.A.)

The results are set out in Table 2 below.

TABLE 2

| | % Ursodeoxycholate Release | | | |
|---|---|---|---|---|
| Time (mins) | URSOFALK | DESTOLIT | ACTIGALL | Example 1 |
| 0 | 0 | 0 | 0 | 0 |
| 5 | 14.5 | 10.1 | 15.5 | 49.2 |
| 10 | 30.0 | 22.8 | 22.5 | 68.5 |
| 15 | 35.2 | 45.8 | 27.5 | 75.7 |
| 30 | 42.7 | 66.4 | 33.5 | 81.3 |
| 45 | 48.0 | 80.8 | 37.8 | 85.1 |
| 60 | 52.9 | 88.8 | 39.1 | 86.0 |

The results shown in Table 2 demonstrate that, not only can effective dissolution of the formulations of the invention be achieved, but that the rate of the dissolution may be superior to that of other formulations containing ursodeoxycholic acid.

EXAMPLE A

Indicative Pharmacological Example using Indomethacin

The following pharmacological example indicates the effects of exogenously added bile acids in a single dose study. It is likely that repeated dosing would result in a more stable endogenous bile acid pool and therefore a more reproducible effect on increased bioavailability of indomethacin. Replacing the bile acids in the formulation with ursodeoxycholate would eliminate the potential toxic effect of detergent bile acids.

Manufacture of dosage forms

The bile acid/indomethacin formulations consisted of sugar spheres coated with a mixture of indomethacin and bile acids (Consolidated Chemicals Ltd, Wrexham, UK) filled into size 1 hard gelatin capsules. The drug coating solution was made by dissolving indomethacin and povidone into an alcoholic solution containing bile acids. The weight ratio of bile acids to indomethacin was approx 2:1. This solution was (bottom) sprayed onto sucrose utilizing a UNI-GLATT® fluidized bed (air suspension system). The resulting spheres were then finally coated in the same system with a solution of HPMC in ethanol or enteric-coated using a solution containing HPMC phthalate. In all cases the temperature and air flow in the UNI-GLATT® system were sufficient to evaporate efficiently the solvent used. The final formulations were assayed for indomethacin content by the high-performance liquid chromatography (HPLC) method described by S. K. Cole et al (1992) *Int. J. Pharm.* 80, 63–73 and the capsule fill weight determined accordingly. Capsules were manufactured to contain 50 mg of indomethacin. Dissolution testing was carried out using the procedure outlined in the US Pharmacopoeia XXII monograph for indomethacin capsules.

Clinical study

Ten healthy male and female subjects aged between 18 and 40 years and within ±10% of ideal body weight participated in the study. Subjects were shown to be in good health by a physical examination and a series of hospital laboratory tests. The subjects were asked to abstain from taking any medication for the two weeks before the start of the study and until after the collection of the last blood sample. Alcohol, tea, coffee and other xanthine-containing beverages were prohibited from 24 h prior to the beginning of the study until its completion. Food was withdrawn for 12 h over the night preceding each part of the study. A light breakfast was allowed 3 h post-dose after which time the subjects were allowed to follow their normal daily diets.

The study was of a randomized two-way cross-over design with the subjects receiving either INDOCID® or bile acid/indomethacin formulation with an equivalent dose of 50 mg or indomethacin. The medication was taken with approx. 250 ml of boiled tap water. The zero time blood samples were taken within a 5 min period preceding the administration of the medication. Subsequent samples were taken at 0.5, 1.0, 1.5, 2.0, 2.5, 3.0, 4.0, 6.0, 8.0, 10.0 and 12.0 h. Blood samples were collected into lithium heparin tubes, gently mixed and centrifuged at $2.0 \times 10^3$ g.min within 15min of collection. Separated plasma was transferred into a clean tube and stored at $-20°$ C. After a one week interval, the subjects received the alternative medication and the blood sampling protocol was repeated. Plasma samples were analysed by the HPLC method described by S. K. Cole et al (1992) *Int. J. Pharm.* 80, 63–73. No degradation of indomethacin was detected during the period of storage at $-20°$ C.

The results of the clinical study were evaluated using the observed values of maximum plasma concentration or indomethacin ($C_{max}$) and time to $C_{max}$ ($t_{max}$) The areas under the plasma concentration curves were calculated using the trapezoidal rule. The results were further assessed using a pharmacokinetic assessment for the evaluation of drug delivery systems described by S. K. Cole et al (1992) *Int. J. Pharm.* 80, 63–73 (see FIG. 1). The statistical significance of the results was assessed by confidence intervals and p-values calculated using a paired t-test (SPSS v3.0).

RESULTS

Stability and Dissolution Studies

Two batches of indomethacin and bile acid-coated sugar spheres were manufactured and further coated with either HPMC film coating (to prevent the spheres from aggregating) or an enteric coating containing HPMC phthalate. For clinical trial and dissolution study purposes, the samples were stored below $25°$ C. and used within three months of manufacture. No changes in indomethacin content were detected during this period.

Dissolution studies of encapsulated bile acid/indomethacin spheres coated with HPMC in various pH buffers show that above pH 6.0 indomethacin is rapidly released and solubilized by bile acids. However, it is interesting to note that fairly rapid solubilisation of indomethacin also occurs at pH 5.0 where indomethacin is not usually readily soluble. Formulations with and without enteric coating, were initially incubated at $37°$ C. in a dissolution bath at pH 1.2 for 60 mins. This procedure resulted int he release of approx 10% of the indomethacin from the non-enteric coated formulation.

Indomethacin release from the enteric-coated formulation at pH 1.2 was below the levels detectable by the analytical method used. Replacing the pH 1.2 buffer with pH 7.2 buffer resulted in a rapid release and solubilisation of indomethacin from the enteric-coated spheres 90% release being achieved within 10min. Release of indomethacin from the non-enteric coated formulation was slower reaching 40% after 30 min and 75% after 60 min.

Clinical studies using indomethacin

The pharmacokinetic data for indomethacin in plasma for each of the formulations are shown in Table 3. Mean plasma indomethacin concentrations are listed as a function of time in Table 4.

TABLE 3

Pharmacokinetic Parameters of Indomethacin Using a Bile Acid/Indomethacin Formulation and INDOCID

| Subjects | Cmax ($\mu$g/ml$^{-1}$) | Tmax (h) | INDOCID (A) AUC ($\mu$g h ml$^{-1}$) |
|---|---|---|---|
| 1 | 3.11 | 2.1 | 6.43 |
| 2 | 4.04 | 1.0 | 7.79 |
| 3 | 3.34 | 4.0 | 12.29 |
| 4 | 4.75 | 0.5 | 9.21 |
| 5 | 5.35 | 0.5 | 9.18 |
| 6 | 6.14 | 1.5 | 8.41 |
| 7 | 6.43 | 1.5 | 10.16 |
| 8 | 4.13 | 4.0 | 14.60 |
| 9 | 7.51 | 3.0 | 16.58 |
| 10 | 6.68 | 2.5 | 14.87 |
| Mean | 5.15 | 2.1 | 10.95 |
| SD | 1.50 | 1.3 | 3.45 |
| CV % | 29.0% | 63.0% | 31.1% |

| Subjects | BILE ACID/INDOMETHACIN FORMULATION (B) | | | AUC Ratio B/A |
|---|---|---|---|---|
| 1 | 9.35 | 1.0 | 16.45 | 2.6 |
| 2 | 5.70 | 2.0 | 21.33 | 2.7 |
| 3 | 9.30 | 1.0 | 8.70 | 0.7 |
| 4 | 11.16 | 2.0 | 18.94 | 2.1 |
| 5 | 5.61 | 1.0 | 11.02 | 1.2 |
| 6 | 8.36 | 1.5 | 16.74 | 2.0 |
| 7 | 4.66 | 2.0 | 16.91 | 1.7 |
| 8 | 3.38 | 4.0 | 17.05 | 1.2 |
| 9 | 5.52 | 4.0 | 18.98 | 1.2 |
| 10 | 6.00 | 2.5 | 16.48 | 1.1 |
| Mean | 6.90 | 2.1 | 16.26 | 1.5 |
| SD | 2.50 | 1.1 | 3.75 | |
| CV % | 36.0% | 53.5% | 23.0% | |

95% Confidence Intervals and p-values for the mean of the difference between treatments

| 95% CI | −0.63–4.15 | −0.87–0.97 | 1.71–8.45 |
|---|---|---|---|
| P | 0.131 | 0.904 | 0.010 |

TABLE 4

Summary of Plasma Indomethacin Concentrations from Bile Acid/Indomethacin Formulation and Indocid

| Time | Bile Acid/Indomethacin Formulation ($\mu g\ ml^{-1}$) | | Indocid ($\mu g\ ml^{-1}$) | |
|---|---|---|---|---|
| (h) | Mean | 95% CI | Mean | 95% CI |
| 0 | N.D. | — | N.D. | — |
| 0.5 | 0.59 | 0–1.47 | 1.37 | 0–3.5.7 |
| 1.0 | 2.74 | 0–5.5 | 2.43 | 0.96–3.9 |
| 1.5 | 3.14 | 1.47–4.81 | 2.66 | 1.03–4.29 |
| 2.0 | 4.33 | 2.25–6.41 | 2.18 | 0.98–3.38 |
| 2.5 | 3.73 | 1.76–5.7 | 1.65 | 0.63–2.67 |
| 3.0 | 2.25 | 1.55–2.95 | 2.43 | 0.94–3.92 |
| 4.0 | 1.82 | 1.3–2.34 | 1.79 | 0.41–3.17 |
| 6.0 | 0.66 | 0.07–1.25 | 0.37 | 0–0.78 |
| 8.0 | 0.66 | 0.21–1.11 | 0.47 | 0–0.97 |
| 10.0 | 0.46 | 0.03–0.89 | 0.05 | 0–0.16 |
| 12.0 | 0.05 | 0–0.16 | N.D. | — |

Values are means with 95% Confidence Intervals (CI) for 10 subjects receiving each formulation. Plasma indomethacin levels in $\mu g\ ml^{-1}$ were determined using the solid phase extraction procedure and HPLC assay described by S. K. Cole et al (1992) Int. J. Pharm. 80 63–73. "N. D." represents indomethacin levels in plasma not detectable using the analytical method used.

The confidence intervals for the mean of the differences between treatments was calculated for $C_{max}$, $t_{max}$ and AUC. A paired t-test was used to determine the significance (Table 3). Interestingly, the inter-individual variation with respect to AUC was considerably reduced with the bile acid/indomethacin formulation in comparison to Indocid. This decrease in inter-subject variability was combined with a 50% increase in AUC from 10.95 to 16.26 $\mu g\ ml^{-1}\cdot h^{-1}$. Plasma half-lives for indomethacin with the two formulations were not calculated because of the nature Of the terminal plasma indomethacin values (Table 4) showing the appearance of secondary peaks. In the case of Indocid, the secondary peaks appear after meals at 3 h and 8 h post-dose. These secondary peaks probably result from the emptying of indomethacin, stored in the gall-bladder, into the gastrointestinal tract from where it is recycled into the systemic circulation. The addition of bile acids with indomethacin reduces the incidence of secondary peaks. This is probably due to secondary peaks being masked by the generally enhanced levels of indomethacin in the circulation (see Tables 1 and 2).

The results of the present investigation have is demonstrated that the concomitant administration of bile acids with indomethacin in healthy subjects increases the bioavailability, in terms of total AUC, by about 50% compared to a conventional formulation of the drug. Part of the explanation for this increased bioavailability may be the rapid dissolution of indomethacin, by bile acids, in the rising pH of the duodenum, as predicted on the basis of the dissolution studies. Previous studies have also shown that bile acids enhance the dissolution to indomethacin (S. Miyazaki et al (1979) Chem. Pharm. Bull. 27, 2468–2472), probably by the formation of mixed micelles, S. Miyazaki et al (1981) Int. J. Pharm. 8, 303–310. The absence of bile acid mixed micelles was suggested to be the explanation for the reduced indomethacin levels observed in the plasma of rats undergoing biliary drainage, (S. Miyazaki et al (1980) Chem. Pharm. Bull. 28, 323–326). However, the results of the present study do not provide any statistically significant evidence of a more rapid absorption of indomethacin from the bile acid-containing formulation, compared to Indocid, in terms of $t_{max}$ (Table 3) or in the plasma concentration summary shown in Table 4. There is also little evidence of a substantially increased $C_{max}$ to explain the increased AUC with the bile acid/indomethacin formulation (Table 3).

An alternative explanation for the enhanced bioavailability of indomethacin with bile acids is that they increase the biliary excretion and/or the enterohepatic recycling of the drug. The extent to which indomethacin undergoes enterohepatic recycling (21–41%) in man and animals is well established (D. E. Duggan et al (1972) Pharmacol. Exp. Ther. 181, 563–575, D. E. duggan et al (1975) Biochem. Pharmacol. 25, 1749–1754, K. C. Kwan et al (1975) J. Pharmacokinet. Biopharm. 4, 255–280, D. E. Duggan and K. S. Kwan (1979) Drug Metab. Rev. 9, 21–41). Similarly well documented is the effect of bile acids on increasing the biliary excretion of organic anions (S. Mandiola et al (1972) Surgery 71, 664–674, R. N. Berk et al (1974) Invest. Radiol. 9, 7–15, R. Vonk et al (1974) Naunyn Schmiedeberg's Arch. Pharmacol. 282, 401–410, Y. Delage et al (1975) Gut 16, 105–108, A. Esteller et al (1984) Q. J. Exp. Physiol. 69, 217–225, S. Kanal and K. Kitani (1986) J. Lab. Clin. Med. 108, 601–607). Therefore, it is likely that indomethacin, an organic anion, will be excreted in bile to an extent determined by the size of the circulating bile acid pool in a given individual. This hypothesis, if correct, would explain the extensive inter-subject variation in dose response to a conventional formulation of indomethacin such as INDOCID® since this dose response would relate to the corresponding inter-subject variation in human bile acid pool size. Furthermore, it could be predicted that expanding the human bile acid pool with exogenous bile acids would increase the enterohepatic recycling of indomethacin and therefore, via a "spill-over effect", the systemic bioavailability of the drug. It is likely that individuals with a small circulating bile acid pool, and therefore poor indomethacin bioavailability, would respond with the greatest increase in indomethacin bioavailability to the addition of exogenous bile acids. Interestingly, analysis of the AUC data, based on a method described by S. K. Cole et al (1992) Int. J. Pharm. 80, 63–73 shows the relationship between increased bioavailability of indomethacin with bile acids, compared to Indocid, to have a strong correlation (r=0.769) which would support this idea (FIG. 1).

Previous studies have shown that the incidence of gastrointestinal lesions correlates with the increased enterohepatic recycling of indomethacin (D. E. Duggan et al (1975) Biochem. Pharmacol. 25, 1749–1754). In view of the present findings, it is believed that the extent of enterohepatic recycling of indomethacin correlates with the size of the endogenous bile acid pool of the individual. Thus, the subjects with the largest endogenous bile acid pool would receive a higher than average dose of indomethacin from a standard formulation such as INDOCID®. Stabilizing the bile acid pool within a population, by administering bile acids, would have the effect of increasing the bioavailability of indomethacin in subjects with an initially small endogenous bile acid pool and would therefore allow for a substantial reduction of administered dose while maintaining consistent therapeutic efficacy. It is believed that a dose reduction of up to 50%, compared to standard formulations, would result in a decreased incidence of gastrointestinal side-effects while also reducing the overall chemical load of indomethacin.

I claim:

1. A pharmaceutical composition for oral administration and delivery to the gastrointestinal tract, comprising:

an active compound which normally undergoes biliary excretion and/or enterohepatic recycling, and a bile acid selected from the group consisting of ursodeoxycholic acid, ursodexoycholyl N-carboxymethylglycine, norcholic acid, norursocholic acid, β-muricholic acid, 7-keto-lithocholate taurodehydrocholate, any other bile acid which does not lyse human erythrocytes at a concentration of at least 30 mM, and their amides, esters and salts, wherein the bile acid is not a naturally occurring bile component mixture, and wherein the composition is formulated protectively from the acidic and enzymatic environment of the stomach or such that the gastrointestinal mucosa is protected from any adverse effects of the active compound.

2. A composition as claimed in claim 1, wherein the pharmaceutically active compound is a non-steroidal anti-inflammatory drug (NSAID).

3. A composition, as claimed in claim 2, wherein the is NSAID is indomethacin, paracetamol, ibuprofen, sulindac, tenoxicam or piroxicam.

4. A composition as claimed in claim 2, wherein the NSAID is indomethacin.

5. A composition as claimed in claim 1, wherein the bile acid is optionally amidated ursodeoxycholic acid or a salt thereof.

6. A composition as claimed in claim 1, which comprises a $C_{12}$–$C_{24}$ fatty acid and wherein a portion of the $C_{12}$–$C_{24}$ fatty acid is formulated for non-sustained release on non-parenteral administration and wherein a portion of the $C_{12}$–$C_{24}$ fatty acid and at least a portion of the pharmaceutically active substance are formulated for sustained release on non-parenteral administration.

7. A composition as claimed in claim 6, wherein the $C_{12}$–$C_{24}$ fatty acid is oleic acid.

8. A process for the preparation of a composition as claimed in claim 1, the process comprising admixing the ingredients together.

9. A process as claimed in claim 8, wherein the ingredients are evaporated from a common solvent.

10. A pharmaceutical composition according to claim 1, wherein the bile acid is selected from the group consisting of ursodeoxycholic acid, ursodexoycholyl N-carboxymethylglycine, norcholic acid, norursocholic acid, β-muricholic acid, 7-keto-lithocholate taurodehydrocholate, and their amides, esters and salts.

* * * * *